(12) United States Patent
Ford

(10) Patent No.: US 11,951,082 B2
(45) Date of Patent: Apr. 9, 2024

(54) COMPOSITION OF CHLORHEXIDINE

(71) Applicant: Jacques Ford, Ocala, FL (US)

(72) Inventor: Jacques Ford, Ocala, FL (US)

(73) Assignee: FORD THERAPEUTICS, LLC, Ocala, FL (US)

( * ) Notice: Subject to any disclaimer, the term of this patent is extended or adjusted under 35 U.S.C. 154(b) by 0 days.

(21) Appl. No.: 18/198,369

(22) Filed: May 17, 2023

(65) Prior Publication Data

US 2024/0074994 A1    Mar. 7, 2024

Related U.S. Application Data

(60) Provisional application No. 63/414,761, filed on Oct. 10, 2022, provisional application No. 63/399,920, filed on Aug. 22, 2022.

(51) Int. Cl.

| | | |
|---|---|---|
| A61K 31/155 | (2006.01) | |
| A61K 9/00 | (2006.01) | |
| A61K 31/047 | (2006.01) | |
| A61K 31/245 | (2006.01) | |
| A61K 31/573 | (2006.01) | |

(52) U.S. Cl.
CPC .......... *A61K 31/155* (2013.01); *A61K 9/0014* (2013.01); *A61K 31/047* (2013.01); *A61K 31/245* (2013.01); *A61K 31/573* (2013.01)

(58) Field of Classification Search
CPC .................................. A61K 31/00; A61K 9/00
See application file for complete search history.

(56) References Cited

U.S. PATENT DOCUMENTS

| | | | |
|---|---|---|---|
| 5,912,007 A * | 6/1999 | Pan ...................... | A61K 9/0056 424/440 |
| 6,495,602 B1 * | 12/2002 | Bhagwat ............... | A61K 31/167 424/602 |
| RE39,264 E | 9/2006 | Harmenberg et al. | |
| 8,603,550 B1 | 12/2013 | Fusco | |
| 8,617,647 B2 | 12/2013 | Feldstein et al. | |
| 9,089,481 B2 | 7/2015 | Singh et al. | |
| 10,449,348 B2 | 10/2019 | Paunescu et al. | |
| 2003/0170324 A1 | 9/2003 | Tritsch et al. | |
| 2004/0033982 A1 | 2/2004 | Katz et al. | |
| 2004/0071757 A1 | 4/2004 | Rolf | |
| 2006/0210516 A1 | 9/2006 | Mower | |
| 2008/0031979 A1 | 2/2008 | Saliou et al. | |
| 2008/0175925 A1 | 7/2008 | Oxford | |
| 2011/0288123 A1 | 11/2011 | Kisak et al. | |
| 2013/0217741 A1 | 8/2013 | Armstrong et al. | |

FOREIGN PATENT DOCUMENTS

| | | | |
|---|---|---|---|
| CA | 2943179 C | | 5/2022 |
| CN | 101208128 B | | 4/2011 |
| CN | 101384261 B | | 12/2011 |
| CN | 102711905 B | | 6/2015 |
| CN | 106132401 A | | 11/2016 |
| CN | 106421180 A | * | 2/2017 |
| CN | 103751194 B | | 1/2018 |
| CN | 106456476 B | | 8/2019 |
| WO | 19950319801 A1 | | 11/1995 |
| WO | 2022034234 A1 | | 2/2022 |

OTHER PUBLICATIONS https://www.drugs.com/mtm/chlorhexidine gluconate-oral-rinse.html.
https://www.hopkinsmedicine.org/health/conditions-and-diseases/herpes-hsv1-and-hsv2/.
ttps://www.mayoclinic.org/diseases-conditions/genital-herpes/diagnosis-treatment/drc-20356167.
https://www.healthline.com/health/drugs/acyclovir-oral-tablet#side-effects.
https://www.healthline.com/health/drugs/valacyclovir-oral-tablet#side-effects.
Park et al., "Effect of chlorhexidine on the in vitro and in vivo herpes simplex virus infection," Oral Surg Oral Med Oral Pathol. Feb. 1989;67(2):149-53. doi: 10.1016/0030-42.
Bailey et al., "Virucidal activity of chlorhexidine on strains of Herpesvirus hominis, poliovirus, and adenovirus," J Clin Pathol. Jan. 1972; 25(1): 76-78.
Fernandez et al, "Virucidal efficacy of chlorhexidine: a systematic review," Odontology Apr. 2022;110(2):376-392.
PCT Notification of the International Search Report and the Written Opinion of the International Searching Authority, or the Declaration, Form PCT/ISA/220, PCT/US2023/030009 (dated Oct. 31, 2023).

* cited by examiner

*Primary Examiner* — Nannette Holloman
(74) *Attorney, Agent, or Firm* — Braun IP Law, LLC; Romulo H. Delmendo

(57) ABSTRACT

The present invention is directed to a medicinal composition, and more particularly, to a composition of chlorhexidine to treat lesions, particularly lesions caused by cold sores and herpes. The composition comprises chlorhexidine as the active ingredient. The composition also comprises a component for pain relief and a component for anti-inflammation. These three components, which act efficaciously in concert, are then combined with a suitable emollient or vehicle to form a topical formulation effective to treat the symptoms of cold sores and herpes. The composition may be formulated as an over-the-counter (OTC) topical formulation.

20 Claims, 1 Drawing Sheet

Compositional Makeup of Medicinal Composition of Chlorhexidine

| Compositional Ingredient(s) | Amounts |
|---|---|
| Chlorhexidine | Effective amount greater than 0 to any amount below prescription strength for the entire composition |
| Hexylresorcinol | Effective amount greater than 0 to any amount below prescription strength for the entire composition |
| Hydrocortisone | Effective amount greater than 0 to any amount below prescription strength for the entire composition |
| Emollient (e.g., 3gm cholesterol N.F., 3gm stearyl alcohol N.F., 8gm wax, white N.F. beadlets (bees wax), and 86gm petrolatum, white USP) | Any suitable amount relative to the active ingredients (e.g., chlorhexidine, benzocaine, and hydrocortisone) |

COMPOSITION OF CHLORHEXIDINE

CROSS-REFERENCE TO RELATED APPLICATION(S)

This application claims the benefit of U.S. Provisional Patent Application No. 63/399,920, filed Aug. 22, 2022, and U.S. Provisional Patent Application No. 63/414,761 filed Oct. 10, 2022, the entire contents of both of which are incorporated herein by reference.

FIELD OF THE INVENTION

The present invention relates generally to a medicinal composition, and more particularly, to a composition of chlorhexidine to treat lesions, particularly lesions caused by cold sores and herpes.

BACKGROUND OF THE INVENTION

Cold sores—also known as fever blisters—are caused by the herpes virus (herpes simplex virus type 1 or HSV-1) and affect a large percentage of the general population. According to Johns Hopkins Medicine, 50 to 80 percent of adults in the United States have oral herpes, which can be spread through intimate contact with someone infected with the virus. See generally https://www.hopkinsmedicine.org/health/conditions-and-diseases/herpes-hsv1-and-hsv2/. According to Johns Hopkins Medicine, the U.S. National Institutes of Health estimates that about 90 percent of adults have been exposed to the virus by age 50. Globally, the World Health Organization (WHO) reports that an estimated 3.7 billion people under age 50 (67%) have HSV-1 infection.

According to Johns Hopkins Medicine, the initial infection of oral herpes is usually the worst, and may be accompanied by severe, flu-like symptoms, including swollen lymph nodes and headache. During the initial infection, sores can occur on and around the lips and throughout the mouth. Certain infected individuals, however, are asymptomatic.

Recurring infections tend to be much milder, with the sores usually erupting on the edges of the lips. Some people do not experience any additional outbreaks beyond the initial infection. The most common signs and symptoms of a recurring oral herpes simplex virus infection include: redness, swelling, heat/pain or itching in the area where the infection will erupt; and painful, fluid-filled blisters appearing on the lips or under the nose, with the blisters and fluid being highly contagious and the blisters eventually becoming sores. About four to six days after the formation of sores, the sores will start to crust over and heal.

Johns Hopkins Medicine lists various treatments for cold sores such as: (i) keeping the infected area clean and dry; (ii) taking antiviral oral medications, such as acyclovir (ZOVIRAX), famciclovir (FAMVIR), and valacyclovir (VALTREX); applying antiviral topical ointments that include acyclovir and penciclovir; and (iii) using over-the-counter topical anesthetics or anti-inflammatory agents to alleviate symptoms. Unfortunately, there is no known cure for cold sores.

Genital herpes, by contrast, is a sexually-transmitted disease that may be caused by the same virus, HSV-1, causing common cold sores and also by herpes simplex virus, type 2 (HSV-2). Genital herpes can cause blisters and open sores (lesions) in the genital area. It can also be asymptomatic for some individuals, but viral shedding may still occur. According to Johns Hopkins Medicine, about 1 in every 6 people ages 14 to 49 in the United States have genital herpes, and according to the U.S. Centers for Disease Control (CDC), new genital herpes infection in 2018 was estimated to be 572,000. The WHO reports that an estimated 491 million people aged 15-49 (13%) worldwide have HSV-2 infection.

When symptoms do occur, genital herpes lesions typically appear as one or more vesicles or small blisters, on or around the genitals, rectum, or mouth. According to the CDC, the average incubation period for an initial herpes infection is 4 days (but may range from 2 to 12 days) after exposure. The vesicles or blisters break and leave painful ulcers that may take two to four weeks to heal after the initial herpes infection. Recurrence can occur, although they may be shorter in duration and/or less severe.

Like common cold sores, there is no known cure for genital herpes. Understandably, there may be social stigma attached to an outbreak of either HSV-1 or HSV-2 infection (e.g., when a patient develops a visible lesion or sore on the lips during an outbreak). The sense of embarrassment, as well as pain and discomfort, could last for many days-even weeks-until the lesions clear and heal completely. For many teenagers or young adults, it may be difficult for them to discuss their infection with an adult or a doctor.

Treatment with prescription antiviral medications, such as acyclovir or valacyclovir, may help sores heal sooner during an initial outbreak, lessen the severity and duration of symptoms in recurrent outbreaks; reduce the frequency of recurrence; and minimize the chance of transmitting the herpes virus to another. See https://www.mayoclinic.org/diseases-conditions/genital-herpes/diagnosis-treatment/drc-20356167. Unfortunately, however, antiviral medications (e.g., acyclovir or valacyclovir) for alleviating cold sores and herpes symptoms are available by prescription only. More importantly, these medications can cause various side effects including nausea, vomiting, diarrhea, headache, weakness, and, in certain instances, even liver problems or, in some severe instances, kidney failure. See, for example, https://www.healthline.com/health/drugs/acyclovir-oral-tablet#side-effects and https://www.healthline.com/health/drugs/valacyclovir-oral-tablet#side-effects.

Chlorhexidine has the molecular formula $C_{22}H_{30}Cl_2N_{10}$ (CAS Registry No.® 55-56-1) and is represented by the following structure:

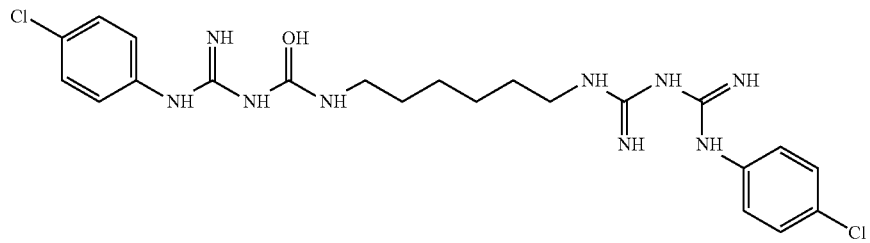 [SMILES: N=C(NCCCCCCNC(=O)NC(=N)Nc1ccc(Cl)cc1)NC(=N)Nc1ccc(Cl)cc1]

Chlorhexidine is also commonly known by its salt forms such as, for example, chlorhexidine gluconate and chlorhexidine digluconate (CHG). Another salt form is chlorhexidine acetate.

Chlorhexidine gluconate is sometimes represented by the following structure:

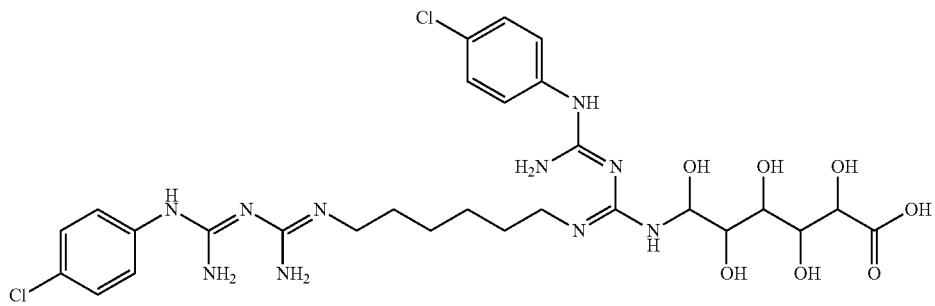 [SMILES: NC(=N\CCCCCC/N=C(\N=C(/N)Nc1ccc(Cl)cc1)NC(O)C(O)C(O)C(O)C(O)C(=O)O)/N=C(\N)Nc1ccc(Cl)cc1]

Chlorhexidine digluconate (CAS Registry No.® 18472-51-0) has the molecular formula $C_{34}H_{54}Cl_2N_{10}O_{14}$ and has the following structure:

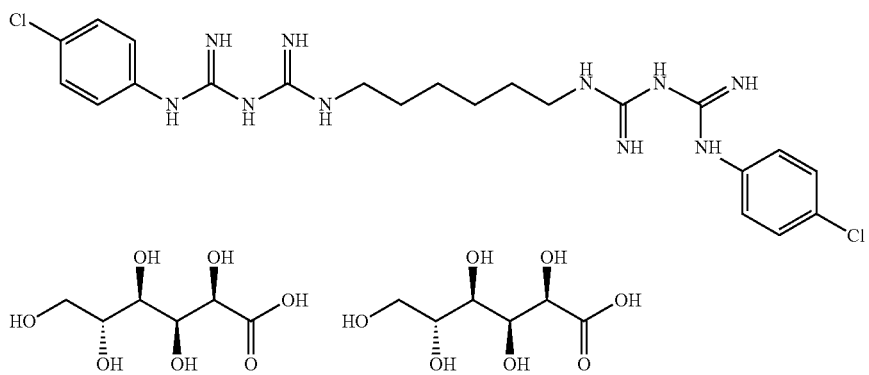

However, the active ingredient in both chlorhexidine gluconate and chlorhexidine digluconate is the same, namely chlorhexidine.

Chlorhexidine has been used for medical purposes since the 1950s. For example, chlorhexidine has been used as a disinfectant and antiseptic for skin disinfection before surgery and for sterilizing surgical instruments. It has also been used for cleaning wounds, preventing dental plaque, treating yeast infections of the mouth, and keeping urinary catheters from blocking. Other uses include cosmetics (additive to creams, toothpaste, deodorants, and antiperspirants), and pharmaceutical products (preservative in eye drops, active substance in wound dressings, and antiseptic mouthwashes).

Furthermore, chlorhexidine is used in veterinary medicine. For example, chlorhexidine is used for topical disinfection of wounds and for managing skin infections in animals. Chlorhexidine-based disinfectant products are also used in the dairy farming industry.

One previous study states that chlorhexidine "moderately, but significantly, inhibited the replication and cytolytic activity of HSV-1 in Vero cell monolayers" and that "[w]hen 0.2% [chlorhexidine] was applied topically onto the HSV-1 infected forehead skin of mice, the development of viral lesions and the viral titers in the skin and trigeminal ganglia were also moderately reduced" (See J. B. Park and N. H. Park, "Effect of chlorhexidine on the in vitro and in vivo herpes simplex virus infection," *Oral Surg Oral Med Oral Pathol.* 1989 February; 67(2):149-53. doi: 10.1016/0030-4220(89)903204. PMID: 2537483). See also Andrew Bailey and Maurice Longson, "Virucidal Activity of Chlorhexidine on Strains of Herpesvirus *Hominis*, Poliovirus, and Adenovirus," *J. Clin. Path.*, 1972, 25, 76-78.

However, a more recent source states that chlorhexidine gluconate "will not treat a viral or fungal infection such as cold sores . . . ." See https://www.drugs.com/mtm/chlorhexidine-gluconate-oral-rinse.html. See also Fernandez et al., "Virucidal Efficacy of Chlorhexidine: A Systematic Review," 110 *Odontology* 376-92 (2022); https://doi.org/10.1007/s10266-021-00660-x.

In view of the foregoing state of the art, there remains a need in the art for an effective medicinal composition or formulation for treating cold sores or herpes symptoms.

There also remains a need in the art for an effective solution to address the problem of providing access to an effective medicinal composition or formulation for treating cold sores or herpes symptoms without the need for a prescription and as an over-the-counter (OTC) product.

There also remains a need in the art to provide a safe and effective solution to address the problem of significantly reducing the time period of a cold sores or herpes outbreak.

There also remains a need in the art for a solution to the problem of providing a medicinal composition or formulation without the serious side effects that may occur in using traditional, prescription antiviral compositions for treating cold sores or herpes.

There also remains a need in the art to provide a safe and effective, OTC topical formulation for treating cold sores or herpes symptoms.

One or more of the foregoing needs, as well as other needs, may be fulfilled by the invention described below.

SUMMARY OF THE INVENTION

The present invention is directed to a medicinal composition, and more particularly, to a composition of chlorhexidine to treat lesions, particularly lesions caused by cold sores and herpes. The composition comprises chlorhexidine as the active ingredient. The composition also comprises a component for pain relief and a component for anti-inflammation. These three components, which act efficaciously in concert, are then combined with a suitable emollient or vehicle to form a topical formulation effective to treat the symptoms of cold sores and herpes. The composition may be formulated as an over-the-counter (OTC) topical formulation.

In a first implementation of the invention, the medicinal composition according to an embodiment of the present invention may comprise:
(a) chlorhexidine;
(b) a pain reliever;
(c) an anti-inflammatory; and
(d) an emollient.

In another implementation, a remedy for treating cold sores or herpes infection, may comprise a composition of ingredients including chlorhexidine gluconate solution, benzocaine, hydrocortisone, cholesterol N.F., stearyl alcohol N.F., wax, white N.F. beadlets, and petrolatum, white USP, a main active ingredient being chlorhexidine, wherein the main active ingredient is an antiviral medication in a concentrated form used to treat cold sores.

In an alternative embodiment, the remedy for treating cold sores or herpes infection, may comprise a composition of ingredients including chlorhexidine gluconate solution, hexyresorcinol, hydrocortisone, cholesterol N.F., stearyl alcohol N.F., wax, white N.F. beadlets, and petrolatum, white USP, In another implementation, the chlorhexidine may be provided as an ingredient to be compounded into the composition in the form of a 4% solution of chlorhexidine gluconate (dye free).

In yet another implementation, the chlorhexidine may be provided as an ingredient to be compounded into the composition in the form of a 2% solution of chlorhexidine gluconate (dye free).

In another implementation, the pain reliever may be provided as an ingredient to be compounded into the composition in the form of a 5% strength benzocaine.

In yet another implementation, the pain reliever may be provided as an ingredient to be compounded into the composition in the form of a 2% strength hexylresorcinol.

In another implementation, the anti-inflammatory may be provided as an ingredient to be compounded into the composition in the form of 1% hydrocortisone.

In another implementation, the emollient may comprise:
(i) cholesterol;
(ii) stearyl alcohol;
(iii) wax, white N.F. beadlets (bees wax); and
(iv) petrolatum.

In another implementation, the medicinal composition according to an embodiment of the present invention may comprise:
(a) a 4% solution of chlorhexidine gluconate (dye free);
(b) a 5% benzocaine pain reliever;
(c) a 1% hydrocortisone anti-inflammatory,
(d) an emollient that may comprise, based on 100 gm total of the emollient, about 3 gm cholesterol N.F., about 3 gm stearyl alcohol N.F., about 8 gm wax, white N.F. beadlets (bees wax), and about 86 gm petrolatum, white USP.

In yet another implementation, the medicinal composition according to an embodiment of the present invention may comprise based on 100 grams (gm):
(a) a 2% solution of chlorhexidine gluconate (dye free);
(b) a 2% hexylresorcinol pain reliever;
(c) a 1% hydrocortisone anti-inflammatory;
(d) an emollient that may comprise, based on 100 gm total of the emollient, about 3 gm cholesterol N.F., about 3 gm stearyl alcohol N.F., about 8 gm wax, white N.F. beadlets (bees wax), and about 86 gm petrolatum, white USP.

In another implementation, the amounts of the active ingredients in the medicinal composition are less than those that would require a prescription.

BRIEF DESCRIPTION OF THE DRAWINGS

The preferred embodiments of the invention will hereinafter be described in conjunction with the appended drawing(s) provided to illustrate and not to limit the invention, where like designations denote like elements, and in which:

FIG. 1 presents a table of ingredients and range of amounts for the medicinal composition comprising chlorhexidine.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As exemplified in the table shown in FIG. 1, the sole FIGURE, the present invention is directed toward a medicinal composition for treating cold sores or herpes comprising chlorhexidine as a main active ingredient.

Referring to FIG. 1, a medicinal composition for treating cold sores or herpes may comprise, as active ingredients, chlorhexidine, a pain reliever, and an anti-inflammatory, all mixed together with an emollient. The main active ingredient is chlorhexidine.

Thus, a remedy for treating cold sores or herpes infection (i.e., a medicinal composition) according to an embodiment of the present invention may comprise a composition of ingredients including chlorhexidine gluconate solution, benzocaine, hydrocortisone, cholesterol N.F., stearyl alcohol N.F., wax, white N.F. beadlets, and petrolatum, white USP, a main active ingredient being chlorhexidine, wherein the main active ingredient is an antiviral medication in a concentrated form used to treat cold sores.

In an alternative embodiment, the remedy can be such wherein the benzocaine is replaced with hexylresorcinol.

In one aspect, the chlorhexidine main active ingredient may be added into the composition in salt form, for example, chlorhexidine gluconate. A 4% solution of chlorhexidine gluconate (dye free) is particularly effective in formulating the composition. In an alternative embodiment, a 2% solution of chlorhexidine gluconate (dye free) can be used.

In another aspect, any pain reliever may be added to formulate the medicinal composition. However, 5% benzocaine is particularly useful, especially when added together with the other active ingredients, to alleviate any pain that may accompany the lesions that one may experience during a cold sores or herpes breakout. However, in an alternate embodiment, benzocaine can be replaced with 2% hexylresorcinol.

In another aspect, any anti-inflammatory may be added to formulate the medicinal composition. However, 1% hydrocortisone, when added together with the other active ingredients, provides excellent results.

All three active ingredients—i.e., chlorhexidine (or its salt), pain reliever (benzocaine or alternatively, hexylresorcinol), and anti-inflammatory (hydrocortisone)—are added into the medicinal composition in amounts less than those that would require a prescription from a medical practitioner. Thus, the medicinal composition according to the present invention provides an advantage and a solution to a problem of being a readily available medication without any potential embarrassment that may otherwise be experienced by a person infected with the herpes virus and is in need of treatment following a breakout of lesions.

The emollient can be any suitable vehicle for a topical application on human skin. In one aspect, an emollient that is the same as or similar to AQUAPHOR® may be used. Based on 100 grams of emollient, the emollient can comprise about 3 gm cholesterol N.F., about 3 gm stearyl alcohol N.F., about 8 gm wax, white N.F. beadlets (bees wax), and about 86 gm petrolatum, white USP. However, other amounts for each component of the emollient may also be suitable for purposes of the present invention.

Thus, an exemplary medicinal composition according to an embodiment of the present invention may comprise:
(a) a 4% solution of chlorhexidine gluconate (dye free);
(b) a 5% benzocaine pain reliever;
(c) a 1% hydrocortisone anti-inflammatory; and
(d) an emollient that may comprise, based on 100 gm total of the emollient:
(i) about 3 gm cholesterol N.F.;
(ii) about 3 gm stearyl alcohol N.F.;
(iii) about 8 gm wax, white N.F. beadlets (bees wax); and
(iv) about 86 gm petrolatum, white USP.

An alternative exemplary medicinal composition according to an embodiment of the present invention may comprise:
(a) a 2% solution of chlorhexidine gluconate (dye free);
(b) a 2% hexyl resorcinol pain reliever;
(c) a 1% hydrocortisone anti-inflammatory; and
(d) an emollient that may comprise, based on 100 gm total of the emollient:
(i) about 3 gm cholesterol N.F.;
(ii) about 3 gm stearyl alcohol N.F.;
(iii) about 8 gm wax, white N.F. beadlets (bees wax); and
(iv) about 86 gm petrolatum, white USP.

A convenient way to incorporate the active ingredients (a) through (c) above is to substitute some of one or more of the components in the emollient, in particular the petrolatum component, with the desired amounts of each of the active ingredients.

In one non-limiting example the 86 gm of the petrolatum component (dxiv) can have anywhere from 1 gram to 20 grams, preferably from 2 grams to 15 grams, and most preferably from 3 grams to 10 grams, thereof, replaced with any one of the active ingredients (a) through (c) above. Thus, the exemplary medicinal composition described above can contain each of components (a)-(c) each in any of the aforementioned ranges of grams. Stated alternatively, the exemplary medicinal composition can contain component (a) in an amount of from 1 weight percent to 20 weight percent; component (b) in an amount of from 1 weight percent to 20 weight percent; and, component (c) in an amount of from 1 weight percent to 20 weight percent, and component (d)(i) can be present in an amount of about 3 weight percent, component (d)(ii) can be present in about 3 weight percent, component (d)(iii) can be present in about 8 weight percent and component d(iv) can be present in an amount of about 26 weight percent.

When the above medicinal composition according to the present invention is applied to patients who are suffering from lesions caused by cold sores or herpes for a total of, for example, three days, it may be possible that the lesions may be resolved in a relatively short period of time (e.g., as short as about 5 days).

Additionally, a significant advantage of the present invention is that the medicinal composition is non-irritating and is suitable for topical application on human skin. As discussed above, existing medication for cold sores or herpes can cause various side effects including nausea, vomiting, diarrhea, headache, weakness, and, in certain instances, even liver problems or, in some severe instances, kidney failure.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claim(s) and their legal equivalents.

What is claimed is:

1. A medicinal composition for treating cold sores or herpes comprising:
(a) chlorhexidine as the sole antiviral agent acting against cold sores or herpes virus;
(b) a pain reliever;
(c) an anti-inflammatory; and
(d) an emollient;
wherein the chlorhexidine (a) is present in the medicinal composition in an amount effective to reduce the time period necessary to treat lesions caused by said cold sores or herpes virus, and the medicinal composition is non-irritating and is formulated as a topical application.

2. The medicinal composition of claim 1, wherein the pain reliever is hexylresorcinol.

3. The medicinal composition of claim 1, wherein the pain reliever is 2% hexylresorcinol.

4. The medicinal composition of claim 1, wherein the pain reliever is benzocaine.

5. The medicinal composition of claim 1, wherein the pain reliever is 5% benzocaine.

6. The medicinal composition of claim 1, wherein the chlorhexidine is a 4% solution of chlorhexidine gluconate.

7. The medicinal composition of claim 1, wherein the anti-inflammatory is hydrocortisone.

8. The medicinal composition of claim 1, wherein the anti-inflammatory is 1% hydrocortisone.

9. The medicinal composition of claim 1, wherein the emollient comprises cholesterol, stearyl alcohol, wax white beadlets, and white petrolatum.

10. A medicinal composition for treating cold sores or herpes comprising:
    (a) chlorhexidine gluconate as the sole antiviral agent acting against cold sores or herpes virus;
    (b) hexyl resorcinol;
    (c) hydrocortisone; and
    (d) an emollient which comprises cholesterol, stearyl alcohol, wax and white petrolatum,
    wherein the chlorhexidine (a) is present in the medicinal composition in an amount effective to reduce the time period necessary to treat lesions caused by said cold sores or herpes virus, and wherein the medicinal composition is non-irritating and is formulated as a topical application.

11. The medicinal composition of claim 10, wherein the hexyl resorcinol is 2% hexyl resorcinol and is present in an amount of from about 1 weight percent to about 20 weight percent based on the total weight of the medicinal composition.

12. The medicinal composition of claim 10, wherein the hydrocortisone is 1% hydrocortisone and is present in an amount of from about 1 weight percent to about 20 weight percent based on the total weight of the medicinal composition.

13. The medicinal composition of claim 10, wherein the cholesterol is present in an amount of from about 1 weight percent to about 5 weight percent based on the total weight of the medicinal composition.

14. The medicinal composition of claim 10, wherein the stearyl alcohol is present in an amount of from about 1 weight percent to about 5 weight percent based on the total weight of the medicinal composition.

15. The medicinal composition of claim 10, wherein the wax is wax white beadlets and is present in an amount of from about 5 weight percent to about 10 weight percent based on the total weight of the medicinal composition.

16. The medicinal composition of claim 10, wherein the white petrolatum is present in an amount of from about 26 weight percent to about 83 weight percent based on the total weight of the medicinal composition.

17. A medicinal composition for reducing the time period necessary to treat lesions caused by cold sores or herpes comprising:
    (a) a 4% solution of chlorhexidine gluconate as the sole antiviral agent acting against cold sores or herpes virus in an amount of from about 1 to about 20 weight percent;
    (b) 2% hexyl resorcinol in an amount of from about 1 to about 20 weight percent;
    (c) 1% hydrocortisone in an amount of from about 1 to about 20 weight percent; and
    (d) an emollient which comprises cholesterol, stearyl alcohol, wax and white petrolatum, and wherein the medicinal composition is non-irritating and is formulated as a topical application.

18. A medicinal composition for reducing the time period necessary to treat lesions caused by cold sores or herpes comprising:
    (a) a 4% solution of chlorhexidine gluconate that is dye free and is the sole antiviral agent acting against cold sores or herpes virus;
    (b) 2% hexyl resorcinol or 5% benzocaine;
    (c) 1% hydrocortisone; and
    (d) an emollient that comprises, based on 100 gm total of the emollient, about 3 gm cholesterol, about 3 gm stearyl alcohol, about 8 gm beeswax, white beadlets, and about 86 gm petrolatum, white and wherein the medicinal composition is non-irritating and is formulated as a topical application.

19. The medicinal composition of claim 18, which is produced by compounding (a) through (c) with emollient (d).

20. The medicinal composition of claim 19, which is produced by substituting a partial amount of one or more ingredients of 100 gm of the emollient (d) with an equal total amount of (a) through (c) to make 100 gm medicinal composition.

* * * * *